United States Patent [19]

Waitz et al.

[11] 4,440,751

[45] Apr. 3, 1984

[54] BROAD SPECTRUM ANTIBIOTIC COMPLEX PRODUCED BY A NOVEL MICROMONOSPORA

[75] Inventors: Jay A. Waitz, Far Hills; Joseph A. Marquez, Montclair; Mahesh G. Patel, Verona; Ann C. Horan, Metuchen, all of N.J.

[73] Assignee: Schering Corporation, Kenilworth, N.J.

[21] Appl. No.: 194,490

[22] Filed: Oct. 6, 1980

[51] Int. Cl.³ ................... A61K 35/00; A61K 31/275; C07C 121/80; C12P 13/02

[52] U.S. Cl. .................................. 424/114; 424/304; 260/465 D; 435/129

[58] Field of Search .............................. 424/114, 304; 260/465 D

Primary Examiner—Jerome D. Goldberg
Attorney, Agent, or Firm—Anita W. Magatti; Carver C. Joyner

[57] ABSTRACT

The novel antibiotic complex designated hazymicin consisting of eight components, is produced by a novel strain of Micromonospora herein designated *Micromonospora echinospora* var. *challisensis* SCC 1411. Also disclosed are the structures of the two components namely, Component 5 and Component 6.

6 Claims, No Drawings

BROAD SPECTRUM ANTIBIOTIC COMPLEX PRODUCED BY A NOVEL MICROMONOSPORA

This invention relates to a novel broad spectrum antibiotic complex, designated hazymicin, two components of which we have isolated, characterized and determined to be novel. More particularly, this invention relates to the production of an antibiotic complex by a novel strain of Micromonospora, herein designated *Micromonospora echinospora* var. *challisensis* SCC 1411. The microorganism is also sometimes referred to as SCC 1411. *M. echinospora* var. *challisensis* was isolated from a soil sample collected in Challis, Idaho. A viable culture of the micoorganism has been made a part of the permanent collection of the Northern Utilizaton and Research Service, U.S. Department of Agriculture, Peoria, Ill., where it was assigned accession number NRRL 12255. A viable culture was also deposited with the American Type Culture Collection (ATCC) where it was assigned accession number 31675. Sub-cultures of *M. echinospora* var. *challisensis* may be obtained from the depositories.

THE MICROORGANISM

*M. echinospora* var. *challisensis* has the following morphologic characteristics when grown in broth after seven days incubation at 30° C. Abundant rough walled spores, 1.0 to 1.5 microns in diameter, are formed along the length of fine 0.5 to 0.8 microns in diameter, slightly branched mycelial strands. Spores occur singly or in clusters and are sessile or on short to long sporophores. Electron microscopic observations of spore whole mounts show protruberances or warts on the spore surface.

The organism contains meso-diaminopimelic acid (meso-DAP) as a characteristic amino acid in the cell wall with arabinose and xylose as characteristic sugar components. These morphologic and chemical characteristics identify SCC 1411 as a species of Micromonospora.

Table 1, sets forth the cultural characteristics of SCC 1411 cultivated on various standard media suggested by Shirling and Gottlieb (Inter. J. Syst. Bact., 16:313-340, 1966) and by Waksman (The Actinomycetes, Vol. II, Williams and Wilkins Co., 1961).

Observations were made after 14–21 days at 30° C.

The color designations assigned to the vegetative mycelial pigments consists of a color name (Descriptive Color Names Dictionary, Container Corp. America, 1950). Also set forth is a color chip number taken form the Color Harmony Manual, ed. 4 Container Corp. America, 1958. The color of SCC 1411 ranges from tan-orange to light rose. A slight white to pink bloom is formed on Potato Dextrose Agar. Diffusable pigments, when formed, are grey-brown to rose.

The carbohydrate utilization and physiologic characteristics of strain SCC 1411 are set forth in Tables 2 and 3, respectfully.

Microscopic and macroscopic appearance of SCC 1411, including the formation of warty spores, vegatative mycelium pigmentation, the occurrence of a bloom, and physiologic characteristics such as growth in the presence of high concentrations of aminoglycoside antibiotics, inability to utilize lactose and fair to poor growth on galactose relates this organism to the *Micromonospora echinospora* group.

SCC 1411 differs from the *M. echinospora* group only in its inability to utilize rhamnose and in the production of the antibiotic complex of this invention. The culture is therefore considered a variety of *M. echinospora* which we designated *M. echinospora* var. *challisensis* SCC 1411.

TABLE 1
GROWTH CHARACTERISTICS OF SCC 1411 ON VARIOUS DESCRIPTIVE MEDIA

| Medium | |
|---|---|
| Bennett's Agar | G: +++, good |
| | S: Raised, convoluted |
| | AM: Absent |
| | DFP: Absent |
| | C: g5nl, chocolate |
| Czapek-Sucrose Agar | G: ++, fair |
| | S: Raised, granular |
| | AM: Absent |
| | DFP: Faint yellow brown |
| | C: g4ne, luggage tan |
| Glycerol-Asparagine Agar (ISP No. 5) | G: +, fair to poor |
| | S: Flat, granular |
| | AM: Absent |
| | DFP: Absent |
| | C: g4gc, rose beige |
| Nutrient Agar | G: +, fair to poor |
| | S: Flat, granular |
| | AM: Absent |
| | DFP: Absent |
| | C: g4ie, cork tan |
| Potato-Dextrose Agar | G: ++, moderate |
| | S: Raised, granular |
| | AM: Present; white-rose bloom |
| | DFP: Absent |
| | C: g5li, dark rose taupe |
| Emerson's Agar | G: +, fair to poor |
| | S: Flat, granular |
| | AM: Absent |
| | DFP: Absent |
| | C: g4ec, light rose beige |
| NZ—Amine Glucose Agar | G: +++, good |
| | S: Raised, deeply folded, waxy |
| | AM: Absent |
| | DFP: Absent |
| | C: g4ne, luggage tan |
| Yeast Extract Glucose Agar | G: +++, good |
| | S: Flat, granular to folded |
| | AM: Absent |
| | DFP: Slight gray brown |
| | C: g5nl, chocolate |
| Tomato-Paste Oatmeal Agar | G: +++, good |
| | S: Raised, plicate |
| | AM: Absent |
| | DFP: Absent |
| | C: g7ni, rose brown |
| Yeast Extract Malt Extract Agar (ISP No. 2) | G: +++ |
| | S: Raised, folded |
| | AM: Absent |
| | DFP: Absent |
| | C: g3ie, camel |
| Oatmeal Agar (ISP No. 3) | G: +, fair to poor |
| | S: Flat, granular |
| | AM: Absent |
| | DFP: Absent |
| | C: g4ic, suntan |
| Inorganic Salts - Starch Agar (ISP No. 4) | G: ++, moderate to fair |
| | S: Flat, granular |
| | AM: Absent |
| | DFP: Absent |
| | C: center, PO, black; periphery, g5ig, rose taupe |
| Starch Agar (Waksman No. 21) | G: +, fair to poor |
| | S: Flat, granular |
| | AM: Absent |
| | DFP: Absent |
| | C: g4ie, cork tan |
| Gelatin Agar (McDade) | G: ++, moderate to fair |
| | S: Flat, granular |
| | AM: Absent |
| | DFP: Absent |
| | C: g2le, mustard |

TABLE 1-continued

GROWTH CHARACTERISTICS OF SCC 1411
ON VARIOUS DESCRIPTIVE MEDIA

| Medium | |
|---|---|
| Casein Agar | G: +, fair to poor |
| | S: Flat, granular |
| | AM: Absent |
| | DFP: Absent |
| | C: g4ge, rose beige |
| Tyrosine Agar (Modified) | G: ++, moderate |
| | S: Raised, slightly folded |
| | AM: Absent |
| | DFP: Present; faint brown |
| | C: g5ng, brick red |
| Starch Agar (Modified) | G: +++, good |
| | S: Raised, plicate |
| | AM: Absent |
| | DFP: Present; slight rose |
| | C: g4lc, dusty orange |

G = Growth; S = Surface characteristics; AM = Aerial mycelium; DFP = Diffusable pigment; and C = Color of the growth.

TABLE 2

CARBOHYDRATE UTILIZATION OF SCC 1411

| Utilization of: | Result |
|---|---|
| D-Arabinose | ±, poor |
| L-Arabonose | +++, good |
| Cellibiose | ++, moderate |
| Dextrin | ++, moderate |
| Dulcitol | ±, poor |
| Erythritol | ±, poor |
| Fructose | +, fair |
| L-Fucose | ±, poor |
| Galactose | +, fair |
| Glucose | +++, good |
| α-m-d-glucoside | ±, poor |
| Inositol | ±, poor |
| Inulin | +, fair |
| Lactose | ±, poor |
| Maltose | +++, good |
| Mannitol | ±, poor |
| Mannose | +++, good |
| Melibiose | ±, poor |
| Melizitose | ±, poor |
| Raffinose | +, fair to poor |
| Rhamnose | ±, poor |
| Ribose | ±, poor |
| Sucrose | +++, good |
| Trehalose | +++, good |
| D-xylose | +++, good |

TABLE 3

PHYSIOLOGIC CHARACTERISTICS OF SCC 1411

| Test | Result |
|---|---|
| Utilization of: | |
| Acetate | + |
| Benzoate | − |
| Butyrate | + |
| Citrate | − |
| Glucuronate | − |
| Glutamate | + |
| Lactate | + |
| Malate | − |
| Propionate | + |
| Pyruvate | + |
| Succinate | − |
| Tartrate | − |
| Growth in the Presence of: | |
| 50 mcg/ml | |
| Gentamicin | + |
| Sisomicin | + |
| Kanamycin | + |
| Erythromycin | − |
| Cycloserine | − |
| Tetracycline | − |
| Gentamicin A | + |

TABLE 3-continued

PHYSIOLOGIC CHARACTERISTICS OF SCC 1411

| Test | Result |
|---|---|
| NaCl | |
| 1.0% | +++, good |
| 2.0% | +, fair to poor |
| 3.0% | ±, poor |
| $Na_2S_2O_3$ | |
| 1.0% | +++, good |
| 2.0% | ±, poor |
| 3.0% | ±, poor |
| Hydrolysis of: | |
| Adenine | − |
| Hypoxanthine | − |
| Tyrosine | + |
| Xanthine | − |
| Chitin | + |
| Casein | + |
| Starch | + |
| DNA | + |
| Gelatin | + |
| Breakdown of: | |
| Urea | − |
| Allantoin | − |
| Growth at: | |
| 27° C. | ++, moderate |
| 35° C. | +++, good |
| 40° C. | +++, good |
| 45° C. | ±, poor |
| 50° C./8 hours | ±, poor |
| Grown on: | |
| Potato + $CaCO_2$ | +++, good |
| Potato − $CaCO_2$ | ±, poor |
| Nitrite to Nitrate | +, weak |

FERMENTATION

The fermentation is preceded by the preparation of an inoculum in a suitable nutrient medium. In general the sterile nutrient medium is inoculated with about 4% by volume of a frozen whole broth of *M. echinospora* var. *challisensis* SCC 1411. For 10 liter fermentations, a second inoculum consisting of about 500 ml is usually required, and for fermentations of 50 liters and 100 liters, a third inoculum stage is usually required. These inocula are usually 2.5 liters and 5.0 liters, respectively.

The fermentation is effected in an aqueous, aerated, agitated, temperature and pH controlled medium containing assimilable sources of carbon and nitrogen. The fermentation is usually conducted at about 30° C., at or in the vicinity of pH 7.0, e.g. 6.8–7.5. A typical fermentation is complete at from about 80 to about 105 hours, the progress of the fermentation being determined by disc or well assays generally used in the art, e.g. against *Sarcina lutea* and *E. coli*.

Suitable media for preparing the inoculum and for the fermentation are the following:

MEDIUM A

| Germination Medium | |
|---|---|
| Beef Extract | 3.0 gm |
| Tryptose | 5.0 gm |
| Dextrose | 1.0 gm |
| Potato Starch | 24.0 gm |
| Yeast Extract | 5.0 gm |
| $CaCO_3$ | 2.0 gm |
| Tap $H_2O$ | 1000 ml |
| Adjust pH to 7.5 with NaOH before sterilization. | |

MEDIUM B

FERMENTATION MEDIUM

| | |
|---|---|
| Yeast Extract | 5.0 gm |
| Dextrose | 10.0 gm |
| Soluble Potato Starch | 20.0 gm |
| N—Z Amine Type A[1] | 5.0 gm |
| $CaCO_3$ | 4.0 gm |
| $CoCl_2$ | $10^{-6}$ M |
| Tap $H_2O$ | 1000 ml |

MEDIUM C

ALTERNATE FERMENTATION MEDIUM

| | |
|---|---|
| Yeast Extract | 5.0 gm |
| Dextrose | 10.0 gm |
| Staley Staclipse "J" Starch[2] | 50.0 gm |
| NZ—Amine Type A[1] | 7.5.0 gm |
| $CaCO_3$ | 4.0 gm |
| $CoCl_2$ | $10^{-6}$ M |
| Tap $H_2O$ | 1000 ml |

[1] Humko Sheffield
1099 Wall Street West
Lyndhurst, New Jersey 07071

[2] A. E. Staley Manufacturing Company
2200 Eldorado Street
Decatur, Illinois 62525

MEDIUM D

ALTERNATE FERMENTATION MEDIUM

| | |
|---|---|
| Yeast Extract | 5.0 gm |
| Dextrose | 10.0 gm |
| Soluble Potato Starch | 20.0 gm |
| Toasted Soy Grits | 5.0 gm |
| $CaCO_3$ | 4.0 gm |
| $CoCl_2$ | $10^{-6}$ M |
| Tap $H_2O$ | 1000 ml |

ISOLATION OF THE HAZYMICIN COMPLEX

When the fermentation has reached peak activity, the antibiotic complex is harvested by extraction with a polar non-water miscible organic solvent, preferably ethyl acetate.

The fermentation mixture is extracted at least twice using two volumes of solvent per volume of whole broth for each extraction. The extracts are combined and concentrated to a residue in vacuo. The residue is dissolved in acetone and added to a six to four (6:4) mixture of ethyl ether:hexane. The resulting precipitate is collected by filtration or centrifugation and dried in vacuo.

The hazymicin complex obtained in this manner consists of about 8 components and some unknown impurities. Component 5 and component 6 are usually the most abundantly produced. On the basis of thin layer chromatography in numerous solvent systems, and subsequent bioautography, the hazymicin complex appears to be different from most other known antibiotics. The seemingly contradictory microbiological activity of the complex set forth hereinbelow also serves to differentiate the antibiotic complex from those known heretofore.

The hazymicin complex obtained above is subjected to thin layer chromatography on silica gel plates using a solvent system consisting of chloroform:methanol (9:1). Bioautography of the plates revealed that the complex consists of at least eight components which are disignated components 1 to 8 based upon decreasing $R_f$ wherein component 1 is proximate to the solvent front and component 8 is proximate to the origin (i.e. is distal to the front).

Separation of Hazymicin Component 5 and Hazymicin Component 6 from the co-produced antibiotics The two major components of the fermentation may be obtained by chromatography on Sephadex LH20, or an equally functioning absorbent, of an ethanol solution of the antibiotics and eluting with ethanol. Fractions active against *Sarcina lutea* are chromatographed on thin layer plates in duplicate using the above noted chloroform: methanol (9:1) solvent system. Detection of the location of the spots is accomplished by exposure of one plate to iodine vapors or to sulfuric acid:methanol (1:1) spray and by bioautography of the duplicate plate against *Sarcina lutea*.

Fractions are combined in accordance with the thin layer chromatographic patterns and concentrated to a residue containing the hazymicin complex. Individual components 5 and 6 are obtained by re-chromatographing the mixture on a silica gel column. The column is eluted with a chloroform:methanol (9:1) solvent system. Detection of the spots is performed as described above. The appropriate fractions are combined and concentrated to yield component 5 and component 6, free from the antibiotics so-produced therewith and free from each other.

THE ANTIBIOTICS

Stability

The Hazymicin complex is stable between pH 6–8 at room temperature and at pH 6–7 up to 100° C. for 15 minutes. It rapidly loses activity at room temperature at pH 2–4 and pH 10 and above.

On the basis of physicochemical analyses, such as infrared spectrometry, PMR, CMR, mass spectrometry, and x-ray crystallography, it was concluded that hazymicin component 5 and hazymicin component 6 have identical empirical formulae i.e. $C_{20}H_{18}O_4N_4$.

Hazymicin, components 5 and 6, also share the following physicochemical constants:

IR (Nujol) 3260, 3300, 3430, 3480, 2155, 2175, 1679 cm$^{-1}$

PMR $\delta$3.0 (m, 4H, Ar—C$\underline{H}_2$); 4.48 (dd, 2H, 7.5, 6.5 Hz, —CH); 6.8 (d, 2H, 8.0 Hz, aromatic); 7.0 (dd, 2H, 8.0, 1.5 Hz, aromatic); 7.08 (d, 2H, 1.5 Hz, aromatic); 7.45 (broad s, 2H, N$\underline{H}$); 7.65 (broad s, 2H, N$\underline{H}$); 8.9 (broad s, 2H, O$\underline{H}$).

CMR 37.7 (t), 58.8 (d), 115.6 (d), 129.0 (d), 132.1 (d), 125.7 (s), 126.0 (s), 153.5 (s), 167.0 (s), 158.0 (s).

In view of the foregoing, it was concluded that hazymicin components 5 and 6 may be represented by the following structural formulae:

Component 5

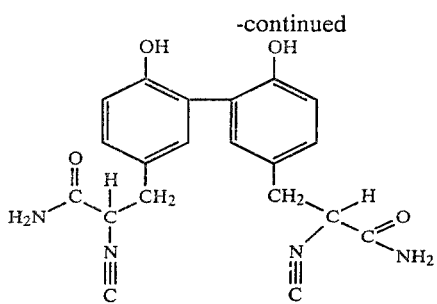

Component 6

The carbon atoms in the side chains of the respective components which are one carbon removed from the benzenoid rings are asymetric (chiral center). Component 5 is a racemic mixture having both chiral centers of the same chirality [i.e., (R), (R) and (S), (S)]. Component 6 has two centers of opposite chirality.

ANTIMICROBIAL PROPERTIES OF HAZYMICIN

The hazymicin complex exhibits in vitro activity against Staphylococcus, Sarcina, Bacillus, *E. coli*, Pseudomonas and Candida. However, the zones of inhibition on agar plates are nearly always hazy, thus the name hazymicin. Broth dilution tests using the same samples used for testing on agar gave high (8 to >64 mcg/ml) MIC values. However, the same material in standard in vivo tests using CF-1 (Carworth Farms) mice gave subcutaneous and oral $PD_{50}$ values of 10–50 mg/kg. against a lethal infection of *Staphyloccus aureus* and *E. coli*. The subcutaneous $LD_{50}$ of the samples was 200 mg/kg. i.e. greater than 4 to 20 times the $PD_{50}$ dose.

In view of its in vitro and in vivo antibacterial activity, the hazymicin complex and the components thereof may be used to disinfect examining rooms and tables used by veterinarians. They may also be used to treat laboratory and domestic animals which have infections caused by susceptible bacteria.

The antibiotics of this invention are preferably administered in admixture with suitable pharmaceutical excipients known to the art. Further, the antibiotics may be used as the complex, or alternatively component 5 and/or component 6 may be used singly or in concert.

The antibiotics of this invention may be used in the form of tablets, capsules, oral suspensions or oral solutions, topical ointments or creams. In oral and parenteral preparations, the antibiotics should be administered in divided doses 1 to 4 times a day which dose should total from 25 to 100 mg/kg/day, the precise dose being left to the practicioner. Ointments and creams should be prepared to contain from about 1% to about 10% of antibiotic and should be applied to the infected areas about 4 to about 6 times per day.

EXAMPLE I

Preparation of Hazymicin Complex

A. First Stage Inoculum

Inoculate 50 ml of sterile Medium A in a 350 ml flask with 2.0 ml of a previously prepared frozen whole broth containing *Micromonospora echinospora* var. *challisensis*. Incubate the inoculated medium at 30° C. for 48 hours on a shaker at about 300 rpm.

B. Second Stage Inoculum

Prepare and sterilize 500 ml of Medium A in a 2 liter Erlenmeyer flask and inoculate with 25 ml of the first stage inoculum. Incubate the inoculated broth under the same conditions described in Step A.

C. Third Stage Inoculum

Prepare and sterilize 10 liters of Medium A in a 14 liter fermentor equipped with an agitator, thermometer an air inlet and exhaust. Inoculate the sterile medium with 500 ml of second stage inoculum prepared in Step B. Incubate the inoculated medium at 30° C. using 0.35 (volume-per-volume per minute (VVM) of air and agitation at about 350 rpm.

D. Fermentation

Prepare and sterilize 100 liters of Medium B in a 150 liter fermentor equipped with agitation, temperature recording means, an air inlet, pH adjustment means, and means for sampling the fermentation. Inoculate the sterile medium with two liters of the inoculum prepared as described in Step C. Adjust the temperature to 30° C. Adjust the aeration to 0.35 VVM of air. Adjust the pH of the inoculated medium to 7.0±0.5 and commence the fermentation with agitation at about 350 rpm. Monitor the antibiotic production by disc or well assays generally used in the art. Also, monitor the pH and the dissolved oxygen, the latter being performed by a probe which dips into the fermentation mixture measures the dissolved oxygen and transmits the measurements to a recording device.

E. Isolation of Hazymicin Complex

When the fermentation has reached peak production of the hazymicin complex, extract the whole broth twice with two volumes of ethyl acetate per volume of whole broth. An additional extract may be used to insure complete extraction. Combine the extracts and concentrate to a residue in vacuo. Dissolve the residue in acetone and precipitate by adding to a mixture of ethylether:hexane (6:4) with agitation. Filter and dry the precipitate at room temperature in vacuo to obtain the hazymicin complex.

F. Isolation of Hazymicin Components 5 and 6 From Antibiotics Coproduced Therewith Dissolve the residue (12 g) from Step E in ethanol and absorb the hazymicin complex on a 1000 ml. column of Sephadex LH20. Elute the column with ethanol collecting 18 ml fractions at 1.8 ml/min. Test each fraction by bioautography against *Sarcina lutea* following thin layer chromatography in a solvent system consisting of chloroform:methanol (9:1) using duplicate plates for each fraction. Expose the second plate from each fraction to iodine vapors or to a sulfuric acid:methanol spray (1:1 v/v). Combine the fractions according to thin layer chromatographic patterns and concentrate to dryness to obtain thereby 2.0 g. of a mixture of hazymicin components 5 and 6.

G. Separation of Hazymicin Components 5 and 6

Absorb 2.0 g. of hazymicin components 5 and 6 on a silica gel column (30" high×3" wide). Elute at the rate of 1 ml/minute using a solvent system consisting of chloroform:methanol (9:1). Collect 15 ml fractions and test each fraction as described in Step F. above. Combine fractions having substantially the same chromatographic pattern and concentrate to a residue to yield thereby:

118 mg—hazymicin component 5
150 mg—hazymicin component 6

We claim:

1. A composition of matter having substantial antibacterial activity produced by cultivating a strain of *Micromonospora echinospora* var. *challisensis* having the identifying characteristics of NRRL 12255 in a pH and temperature controlled aqueous nutrient medium having assimilable sources of carbon and nitrogen under controlled aerobic conditions until a composition of matter having substantial antibiotic activity is produced, which composition of matter yields an antibiotic complex designated hazymicin complex, said composition of matter consisting essentially of a mixture of hazymicin component 5 and hazymicin component 6, wherein said components are represented by the formulae

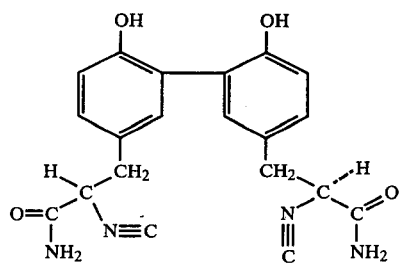

Component 5 and

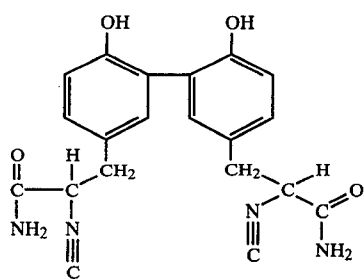

Component 6

2. A compound of claim 1, said compound being Hazymicin component 5 having the formula:

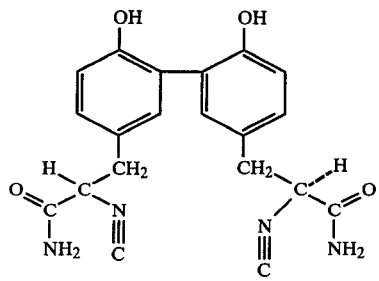

3. A compound of claim 1, said compound being Hazymicin component 6 having the formula:

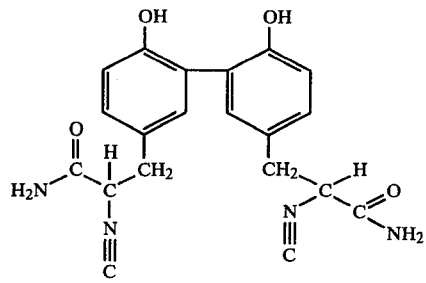

4. A method of eliciting an antibacterial response in a mammal having a bacterial infection which comprises administering to the mammal a therapeutically antibacterially effective dose of the composition of claim 5 as defined in claim 1.

5. The method as defined in claim 4 wherein hazymicin component 5

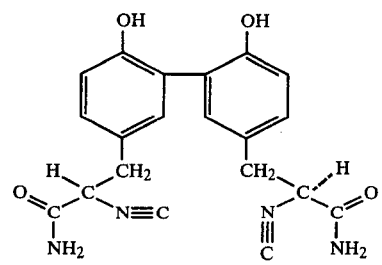

is administered.

6. The method as defined in claim 4 wherein hazymicin component 6

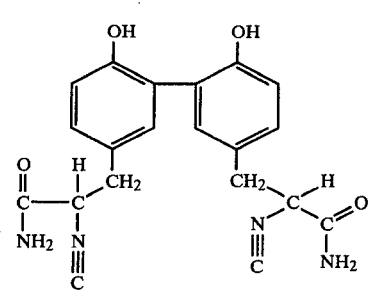

is administered.

* * * * *